United States Patent [19]

Stendahl

[11] Patent Number: 5,909,138
[45] Date of Patent: Jun. 1, 1999

[54] FAST ISOLATED IGBT DRIVER FOR HIGH VOLTAGE SWITCHING CIRCUITRY

[75] Inventor: Gary B. Stendahl, Crystal, Minn.

[73] Assignee: SurVivaLink Corporation, Minneapolis, Minn.

[21] Appl. No.: 08/881,193

[22] Filed: Jun. 24, 1997

Related U.S. Application Data

[60] Provisional application No. 60/021,970, Jun. 27, 1996.

[51] Int. Cl.$^6$ .......................... H03K 17/04; H03K 17/691
[52] U.S. Cl. ............................................. 327/434; 327/389
[58] Field of Search .................................. 327/434–436, 327/437, 389–391

[56] References Cited

U.S. PATENT DOCUMENTS

| | | | |
|---|---|---|---|
| 3,590,322 | 6/1971 | Carr ........................................ | 317/18 D |
| 3,857,398 | 12/1974 | Rubin ................................... | 128/419 D |
| 3,862,636 | 1/1975 | Bell et al. ............................. | 128/419 D |
| 3,886,950 | 6/1975 | Ukkestad et al. ..................... | 128/419 D |
| 4,511,815 | 4/1985 | Wood ..................................... | 327/436 |
| 4,610,254 | 9/1986 | Morgan et al. ........................ | 128/419 D |
| 4,619,265 | 10/1986 | Morgan et al. ....................... | 128/419 D |
| 4,823,796 | 4/1989 | Benson ................................. | 128/419 D |
| 4,906,876 | 3/1990 | Landseadel .............................. | 327/434 |
| 5,019,719 | 5/1991 | King ......................................... | 327/110 |
| 5,097,830 | 3/1992 | Eikefjord et al. .................... | 128/419 D |
| 5,405,361 | 4/1995 | Persson ........................................ | 607/5 |
| 5,434,527 | 7/1995 | Antone ..................................... | 327/434 |
| 5,481,219 | 1/1996 | Jacobs et al. ............................ | 327/434 |
| 5,534,814 | 7/1996 | Archer ..................................... | 327/434 |

FOREIGN PATENT DOCUMENTS

| | | | |
|---|---|---|---|
| WO 95/05215 | 2/1995 | WIPO .............................. | A61N 1/39 |

*Primary Examiner*—Timothy P. Callahan
*Assistant Examiner*—An T. Luu
*Attorney, Agent, or Firm*—Patterson & Keough, P.A.

[57] ABSTRACT

A fast insulated gate bipolar transistor (IGBT) driver circuit for trunking waveforms in external defibrillators is provided. An input circuit is provided to receive input signals. An isolation transformer is provided to isolate the output from the input. A biasing circuit is connected to the isolation transformer for biasing the IGBT. In response to the biasing circuitry, the IGBT rapidly switches between operational states to truncate waveforms at any point during the delivery of energy to a patient.

13 Claims, 6 Drawing Sheets

FAST ISOLATED IGBT DRIVER FOR HIGH VOLTAGE SWITCHING CIRCUITRY

RELATED APPLICATIONS

The present invention claims priority from provisional patent application Ser. No. 60/021,970, filed Jun. 27, 1996 entitled FAST ISOLATED IGBT DRIVER FOR HIGH VOLTAGE SWITCHING CIRCUITRY, which is incorporated herein by reference and is also related to the following co-pending U.S. Patent Applications, all of which are assigned to the assignee of the present invention and all of which are hereby incorporated by reference: PARALLEL CHARGING OF MIXED CAPACITORS, Ser. No. 08/673,804; BIPHASIC DEFIBRILLATION ISOLATION CIRCUIT, U.S. Pat. No. 5,674,266; HIGH VOLTAGE PHASE SELECTOR SWITCH FOR DEFIBRILLATORS, Ser. No. 08/673,195; and HIGH VOLTAGE SERIES DIODE CIRCUIT FOR CAPACITOR CHARGING, Ser. No. 60/020,714.

BACKGROUND OF THE INVENTION

1. Field of the Invention

This invention relates to the field of external defibrillators. In particular, the present invention relates to the switching element drivers used for truncating pulses in a defibrillator.

2. Description of the Related Art:

Cardiac arrest, exposure to high voltage power lines and other trauma to the body can result in heart fibrillation which is the rapid and uncoordinated contraction of the cardiac muscle. The use of external defibrillators to restore the heartbeat to its normal pace through the application of an electrical shock is a well recognized and important tool for resuscitating patients. External defibrillation is typically used in emergency settings in which the patient is either unconscious or otherwise unable to communicate. Time is of the essence since studies have shown that the chances for successful resuscitation diminish approximately ten percent per minute.

Commercially available defibrillators such as those available from SurvivaLink Corporation, the assignee of the present application, are currently configured to produce monophasic waveform defibrillation pulses. Monophasic (i.e., single polarity) pulses such as a damped sine waveform and a truncated exponential waveform have been demonstrated to be effective for defibrillation, and meet standards promulgated by the Association for Advancement of Medical Instrumentation (AAMI). Electrical circuits for producing monophasic waveform defibrillation pulses are generally known and disclosed, for example, in the Persson U.S. Pat. No. 5,405,316 which is assigned to the assignee of the present invention and the disclosure of which is herein incorporated by reference.

The efficacy of biphasic waveform pulses (effectively two successive pulses of opposite polarities) has been established for implantable defibrillators. For example, studies conducted on implantable defibrillators have shown that biphasic waveform defibrillation pulses result in a lower defibrillation threshold than monophasic pulses. A variety of theories have been proposed to explain the defibrillation characteristics of biphasic waveform pulses but no definite conclusions have been reached.

It is anticipated that the efficacy and advantages of biphasic waveform pulses that have been demonstrated in implantable defibrillators will be demonstrated in external defibrillators as well. It has been known to use electromechanical vacuum or gas filled relays to switch the output of storage devices to form biphasic waveforms. These devices are electrically suitable for use in external defibrillators, but pose practical problems in that they are generally fragile, large and very expensive. One important shortcoming is that such devices are not suitable for breaking or interrupting large voltages and currents and, when called upon to do so, often damage the relay contacts. This shortcoming is particularly significant when it is desired to truncate a first portion of a biphasic defibrillation pulse. In such circumstances, to truncate the pulse or waveform without damage to the contacts, it is known to short-circuit the capacitor bank supplying the pulse to be terminated or truncated. Such an approach suffers from the further shortcoming that the energy short-circuited is lost to the system, increasing inefficiency and adding electrical (and mechanical) stress to the components carrying short-circuit current. Thus, there is a continued need for a low cost, compact, and rugged switching circuit.

SUMMARY OF THE INVENTION

The present invention is a fast isolated insulated gate bipolar transistor (IGBT) driver circuit for truncating waveforms in external defibrillators. The IGBTs allow the output waveform to be interrupted at any point in the delivery of energy to a patient. The system of the present invention receives input from a select phase control circuit. An isolation transformed is provided to isolate the output. A biasing circuit is connected to the isolation transformer and at least one IGBT is connected to the biasing circuitry. The at least one IGBT rapidly switches between its operational on and off states in response to the biasing circuitry.

DETAILED DESCRIPTION OF THE INVENTION

The present invention will be described in detail below. In order to fully understand the present invention, a brief discussion of the associated circuitry for an external defibrillator will be given first.

Related Circuitry

Figure 1:
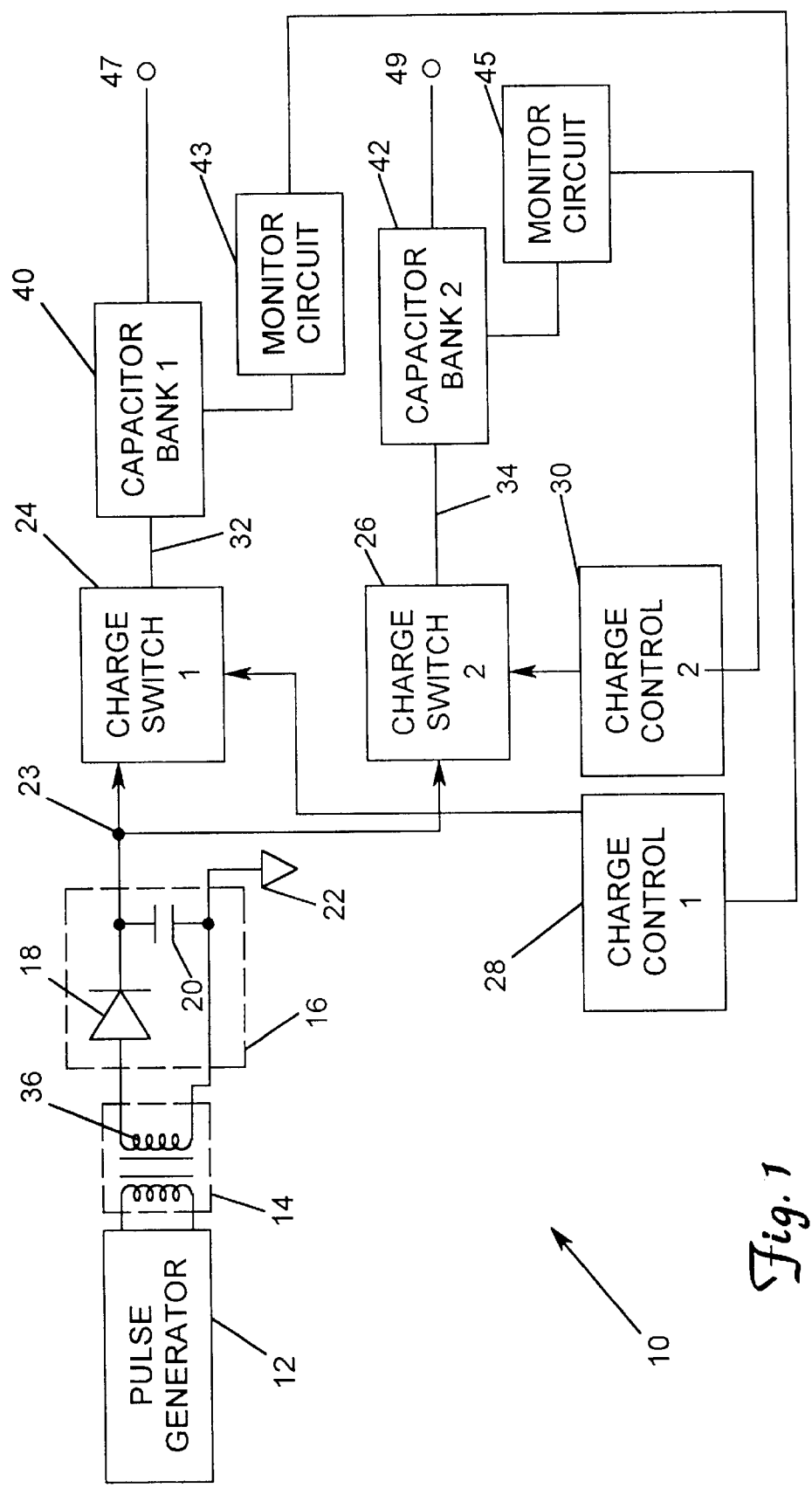
FIG. 1 is a block diagram of a capacitor charge control circuit in accordance with the present invention.

Referring now to FIG. 1, a charge control circuit 10 may be seen. Circuit 10 includes a pulse generator 12 connected to a pulse transformer 14 which is connected to a passive rectifying and filtering circuit 16. Circuit 16 is preferably made up of a high speed (fast recovery) diode 18, which is preferably a UF4007 type, available from General Instruments, and a capacitor 20 which may be in the range of 3–10 microfarads. It should be noted that an active filter is equally acceptable. Circuit common is indicated by an inverted triangle 22, and an output 23 of the rectifying and filtering circuit 16 is connected to first and second charge switches 24, 26. Charge switches 24, 26 are each preferably formed of one or more solid state switching devices such as a silicon controlled rectifier (SCR), a field effect transistor (FET), or an insulated gate bipolar transistor (IGBT). Such devices may be connected in series (to increase voltage capability) or in parallel (to increase current capability) as is well known in the art. Each of the charge switches 24, 26 is controlled by a separate one of a pair of charge control circuits 28, 30.

The respective outputs 32, 34 of the charge switches 24, 26 are individually connected to one of a pair of capacitor banks 40, 42. Output 32 is connected to a first capacitor bank 40, and output 34 is connected to a second capacitor bank 42. This portion of the circuitry will be described in detail with reference to a pair of capacitor banks but it should be noted that additional capacitor banks may also be included without departing from the spirit or scope of the invention. The output of capacitor bank 40 is connected to an electrode terminal 47 and the output of capacitor bank 42 is connected to an electrode terminal 49.

The circuit is designed to output to electrode terminals 47 and 49 a high voltage defibrillation pulse in the range of approximately 2000–3000 volts in the preferred embodiment. It should be noted however that greater or lesser discharge voltages can also be delivered without departing from the spirit or scope of the invention. In order to generate and deliver the voltage levels desired for defibrillation, a two step process is required. The first step is that of charging the capacitors. The second step is that of discharging the capacitors. To charge low cost, reliable capacitors rapidly to the desired voltage levels, the present invention utilizes charge control circuits 28, 30 and charge switch circuits 24, 26 to charge the capacitors in parallel. When connected in parallel, the total capacitance of a particular capacitance bank is the sum of all the capacitors connected in parallel, while the voltage across each of the individual capacitors is equal. To discharge the capacitors to electrode terminals 47, 49, charge control circuits 28, 30 and charge switch circuits 24, 26 configure the capacitors of a capacitor bank in series. This reduces the total capacitance to a fractional value of the individual capacitors and increase the voltage to the sum of the voltages across each individual capacitor.

The capacitor banks are preferably of differing capacitive values or differing voltage capacities. For example, in one embodiment, capacitor bank 40 has a total capacitance of 7200 microfarads while capacitor bank 42 has a total capacitance of 440 microfarads when connected in parallel for charging. Therefore, capacitor bank 42 will charge much more rapidly than will capacitor bank 40. During discharge capacitor bank 40 has a total capacitance of 200 microfarads while capacitor bank 42 has a total capacitance of 110 microfarads while connected in series. It should be noted that many other capacitor banks could be utilized having many different capacitance values, or all having the same capacitance value without departing from the spirit or scope of the invention.

The operation of the charge control circuit 10 is as follows. Pulse generator 12 supplies a series, or train, of preferably square wave pulses, typically at a 50% duty cycle and having an amplitude of approximately 400 volts, at a frequency preferably between 5 KHz and 500 KHz. These pulses have a very rapid rise time. Since the fast rise times and high frequencies of the pulses cause avalanching of most common solid state devices of reasonable cost, the pulses are first passed through passive filter circuit 16. Diode 18 is a fast recovery diode that provides for charging of capacitor 20 and prevents discharge of the capacitor 20 through secondary 36 of pulse transformer 14. Capacitor 20 is preferably selected to be able to absorb and store the energy from at least one charge pulse from pulse generator 12.

As stated above, use of a pulse train with a very rapid rise time on individual pulses is desired, but would lead to avalanche breakdown of standard switches if coupled directly thereto. This would cause the switches to lose control of charging, and may lock the switches on, causing the capacitors to be continually charged until they are destroyed. This consequent loss of charging control is unacceptable. Use of rectifying and filtering circuit 16 avoids such avalanche triggering of solid state switches 24, 26 by keeping high dV/dt values from reaching switches 24, 26, allowing ordinary solid state devices to be used for switches 24, 26.

Figure 2:
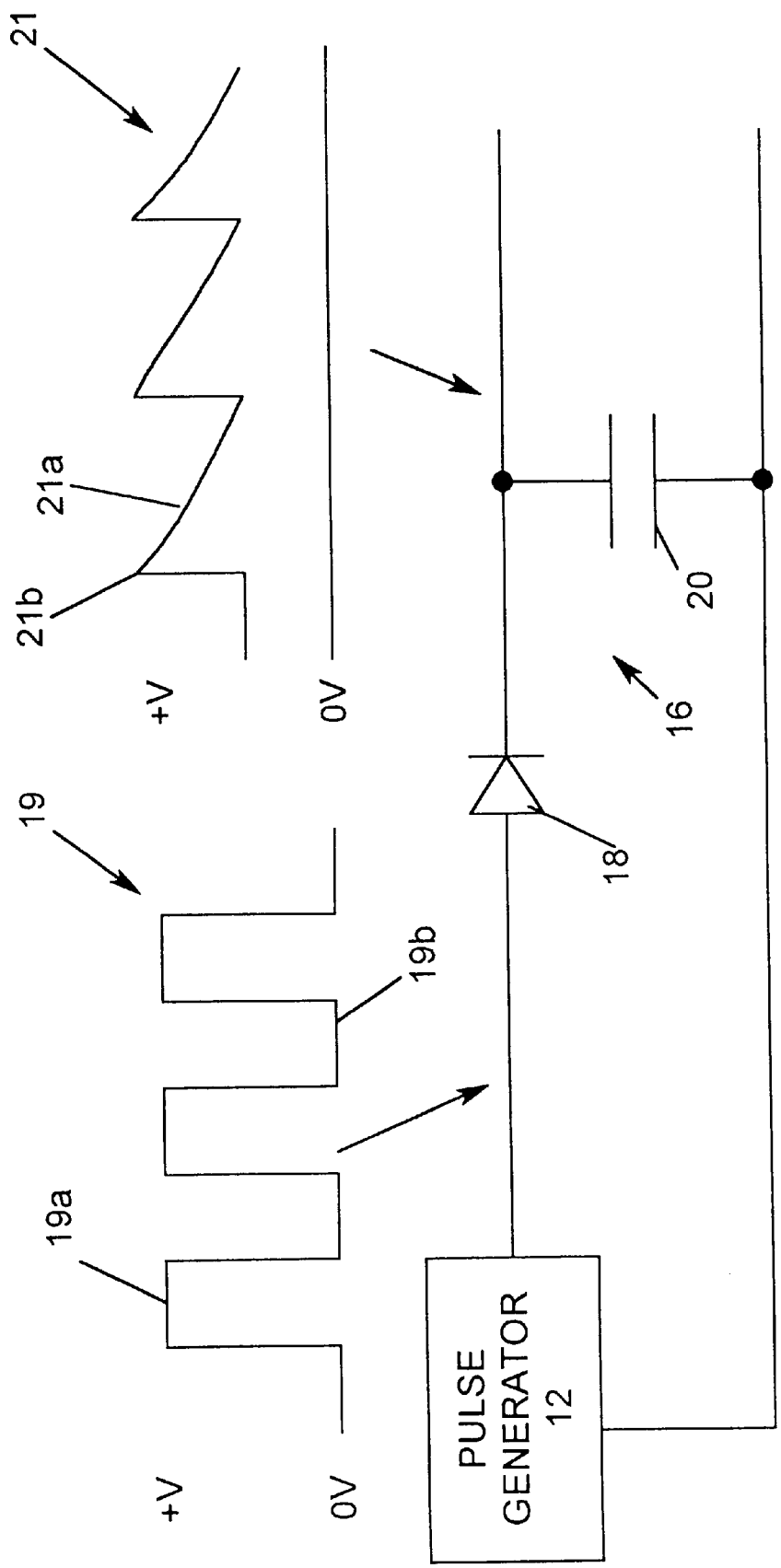
FIG. 2 illustrates a passive filter along with a pictorial representation of a signal before and after the filter.

FIG. 2 illustrates the passive filter along with a pictorial representation of a signal before and after the filter. As can be seen in waveform 19 illustrates the signal coming out of pulse generator 12. This signal is a series of square wave pulses having an amplitude of approximately 400 volts. After passing through filter 16, waveform 21 is obtained which is in the form of a DC level with a generally triangular ripple component. When the ON portion of waveform 19, illustrated at 19a, is seen at diode 18 the diode is forward biased allowing capacitor 20 to charge. Capacitor 20 is charged while diode 18 is forward biased. When signal 19 drops to zero, illustrated at 19b, diode 18 shuts off, halting the charging of capacitor 20. During the off period of diode 18 when the stored energy from capacitor 20 is transferred to the capacitor banks, it's voltage drops slightly causing the triangular ripple voltage illustrated in waveform 21 at 21a. Before capacitor 20 has a chance to discharge the energy stored therein, diode 18 turns back on due to the presence again of a positive voltage from pulse generator 12 causing waveform 21 to rise to a charged level, at 21b.

The DC charge on capacitor 20 is available to each of switches 24, 26 via lead 23 to be distributed to the capacitor banks as needed. It is to be understood that one or both of switches 24, 26 are on during charging. Both switches 24 and 26 may be on together or only one may be on, but at least one must be on during charging. When one or both of switches 24, 26 is on, the charge on capacitor 20 is coupled to the respective one or both of capacitor banks 40, 42.

As previously stated, the value of capacitor 20 is preferably chosen to be able to absorb and store the energy from one pulse. The energy stored in capacitor 20, which is now in the form of a DC level with a generally triangular ripple component, is available to be delivered to either capacitor bank via charge switches 24 or 26. It is also to be understood that the capacitor banks include slower acting diodes (illustrated as D1 et seq. in FIG. 3 of U.S. Pat. No. 5,405,361, the disclosure of which is hereby incorporated by reference). Thus the pulse provided by transformer 14 is not instantly applied to the capacitors and the energy that is not immediately applied is stored in capacitor 20 and continues to be delivered between pulses from generator 12.

Figure 3:
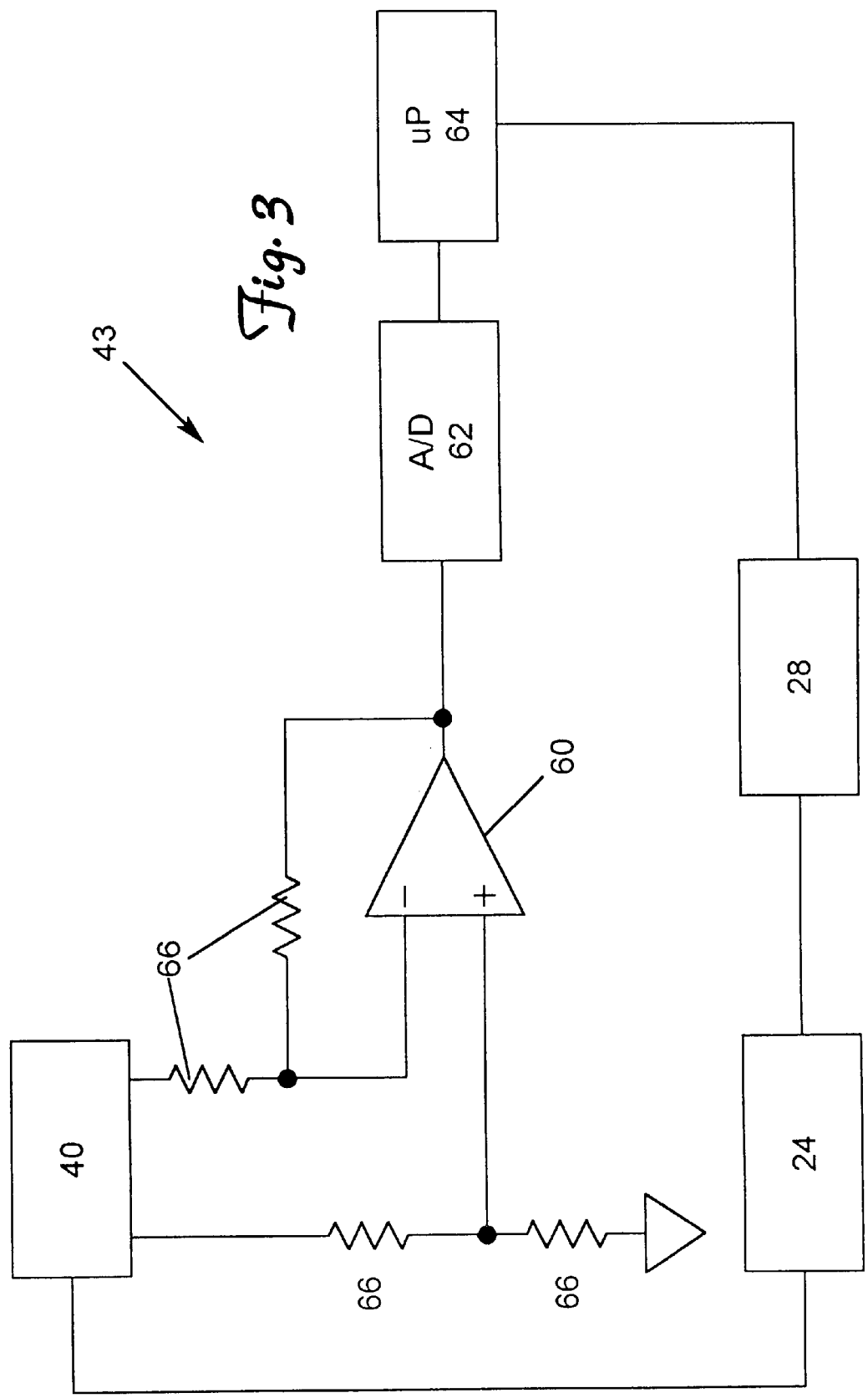
FIG. 3 illustrates one embodiment of a monitoring circuit of the circuit illustrated in FIG. 1.

Circuit 10 also includes voltage monitoring circuits 43, 45 for monitoring the voltage on capacitor banks 40 and 42, respectively. As can be seen in FIG. 1, monitor circuits 43 and 45 are connected to the respective capacitor banks and charge control circuit. Monitoring circuits 43 and 45 are illustrated schematically as block diagrams because there are many different embodiments of monitoring circuits that may be used without departing from the spirit or scope of the invention, such as analog circuitry, digital circuitry and solid state components, for example. FIG. 3 illustrates one preferred embodiment of monitoring circuit 43. It should be noted that monitoring circuit 45 is the same as monitoring circuit 43. As can be seen, an operational amplifier 53 is provided as is an analog to digital converter 55 and a microprocessor 57. Amplifier 60 is connected to capacitor bank 40 via a plurality of resistors 59. In operation, monitoring circuit 43 has a database of preset values stored in microprocessor 57. When capacitor bank 40 reaches the preset value selected in processor 57, charge control circuit 28 is instructed to halt the charging of capacitor bank 40. In an alternative embodiment, microprocessor 57 has the capability of computing an appropriate predetermined value for charging the respective capacitor bank.

When in the charging mode, one or a plurality of capacitor banks may be charged simultaneously. In the embodiment illustrated in FIG. 1 having first and second capacitor banks 40 and 42, if both capacitor banks 40 and 42 are being simultaneously charged, when capacitor bank 42 is fully charged, charge switch 26 is opened as a result of a command from monitoring circuit 45 and all of the charge available at capacitor 20 is then applied to capacitor bank 40 instead of splitting it between the two capacitor banks. When capacitor bank 40 is completely charged, charge switch 24 is opened as a result of a command from monitoring circuit 43. Capacitor banks 40 and 42 are now fully charged and the individual capacitors in each bank are ready to be switched into series for discharge.

Figure 4:
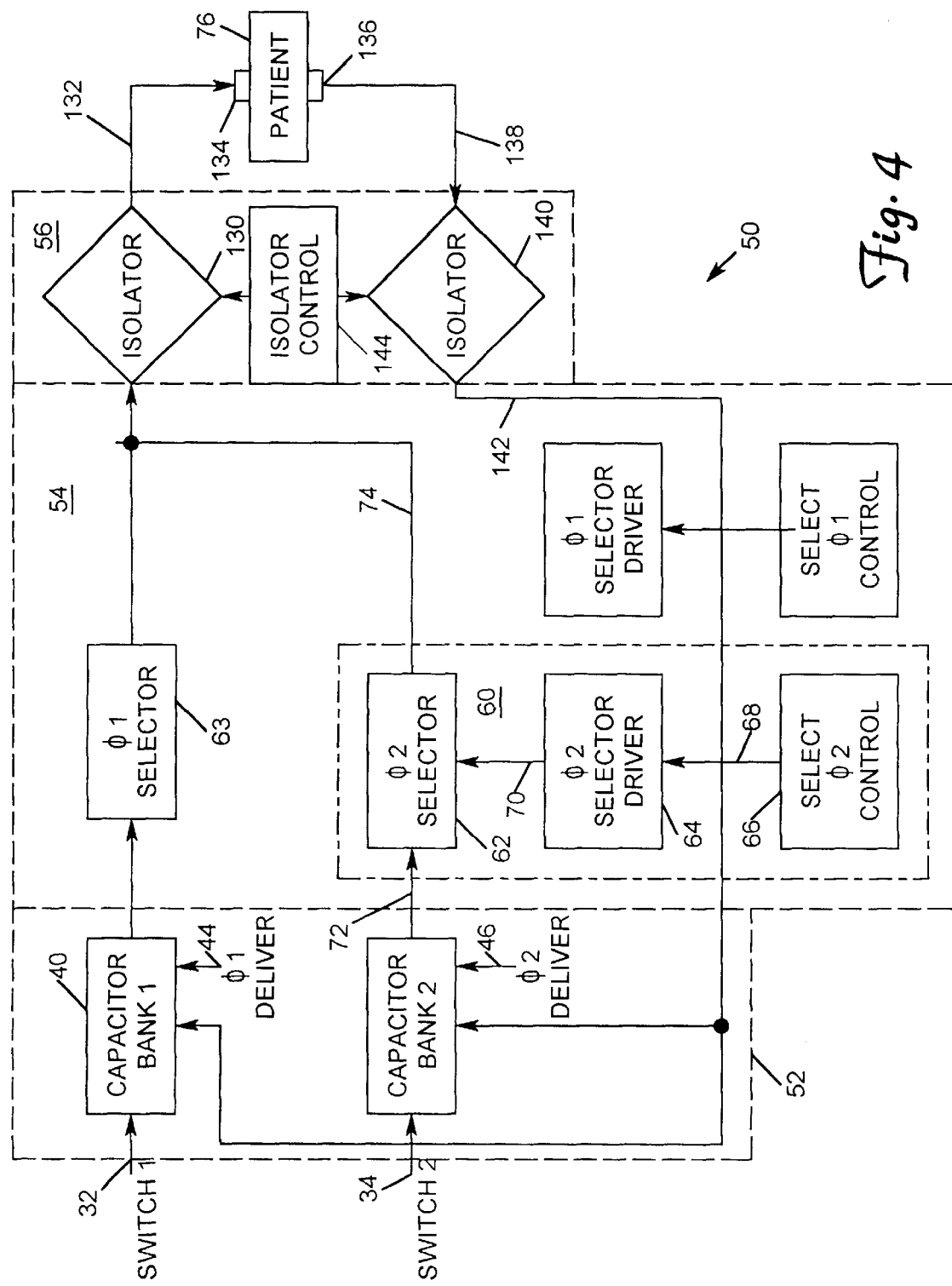
FIG. 4 is a block diagram of a capacitor bank selector and isolation subsystem.

Referring now to FIG. 4, an output circuit 50 suitable for providing biphasic defibrillation pulses may be seen. Output circuit 50 includes a capacitor bank circuit 52, a selector circuit 54, and an isolator circuit 56. The capacitor bank circuit includes first and second capacitor banks 40, 42, each of which have respective phase delivery command lines 44, 46. In the embodiment illustrated, capacitor bank 40 is configured to discharge a positive first phase of the biphasic output pulse while capacitor bank 42 is configured to discharge a negative second phase. It should be noted that additional capacitor banks can be added without departing from the spirit or scope of the invention. Selector circuit 54 has a pair of preferably identical selector subsystems. One subsystem 60 is indicated by a chain line. Subsystem 60 includes a solid state phase selector switch 62 connected to a phase selector driver 64 which in turn is connected to a select phase control 66. It is to be understood that select phase control 66 provides a signal on line 68 to activate and deactivate phase selector driver 64.

When phase selector driver 64 is activated, it drives phase selector switch 62 to a state of conduction (ON) between lines 72 and 74, connecting capacitor bank 42 to isolator circuit 56 and ultimately to a patient when isolator circuit is itself in a conducting state as will be described infra. When select phase control 66 deactivates phase select driver 64, phase selector switch 62 is rendered nonconductive (OFF) between lines 72 and 74, thus stopping any remainder of the portion of a biphasic defibrillation pulse from being delivered from the capacitor bank 42 to a patient 76. It is to be understood that the phase 1 selector subsystem (connected to capacitor bank 40) is formed of the same elements and operates identically to subsystem 60 in the embodiment shown in FIG. 4. To provide a monophasic defibrillation pulse, only the phase 1 selector subsystem is activated, since capacitor bank 40 is connected to provide a positive polarity output and capacitor bank 42 is connected to provide a negative polarity output.

When providing a biphasic defibrillation pulse, it has been found preferable to proceed according to the following sequence:

1. Turn phase 1 selector switch ON, providing a first, positive polarity, exponentially decaying portion of the pulse.
2. Turn phase 1 selector switch OFF, truncating the first portion of the pulse at a desired point.
3. After a time delay, turn phase 2 selector switch ON, providing a second, negative polarity, exponentially decaying portion of the pulse.
4. Turn phase 2 selector switch OFF, truncating the second portion of the pulse at a desired point.

One important aspect of this embodiment is the reduction of the transition time between phase 1 and phase 2. In known systems utilizing SCRs as switching mechanisms, any charge in the capacitors must be reduced below the level of the holding current for the SCR before a phase shift can occur. This can take up to 10 seconds due to the large amount of current typically remaining on the capacitors. This is so even though photoflash capacitors are typically utilized due to their rapid discharge.

In this embodiment, the SCR's have been replaced by IGBT's and photoflash capacitors are no longer needed, allowing cheaper, mass-produced products to be used. The delay of switching between phase 1 and phase 2 depends only on the length of time to shut off phase 1 long enough to allow phase 2 to be energized. This time frame is on the order of microseconds.

Figure 5:
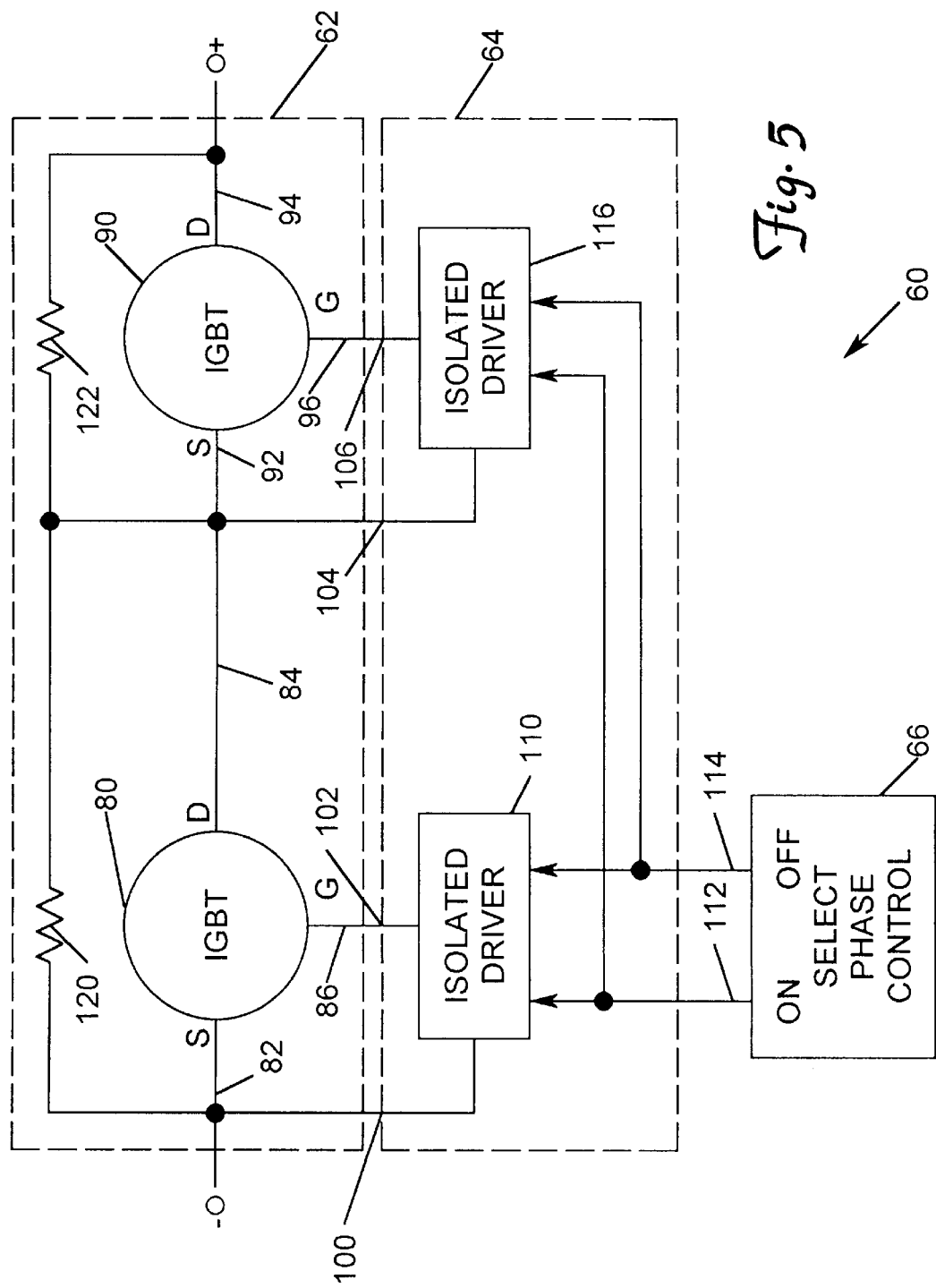
FIG. 5 is a more detailed block diagram of an individual selector, driver and control.

Referring now also to FIG. 5, details of the phase selector switch 62 may be seen. The one embodiment will be described with reference to a pair of IGBT's, but it should be noted that more may be used as will be described below. To withstand the high voltages and high currents encountered in providing defibrillation pulses (whether monophasic or biphasic) two IGBT's are connected in series. A first IGBT 80 has a power input 82 and a power output 84 and a signal input or gate 86. Similarly, a second IGBT 90 also has a power input 92, a power output 94, and a signal input, or gate, 96. Referring now also to FIG. 4, power input 82 is connected to lead 72 carrying the output of capacitor bank 42. Power output 84 is connected to power input 92 and power output 94 is connected to lead 74. The connection 70 between phase selector driver 64 and phase selector switch 62 is actually made up of four connections 100, 102, 104, 106. Connections 100 and 102 couple an isolated driver 110 to IGBT 80. Similarly connection 68 between the select phase control 66 and the phase selector driver 64 actually includes two leads 112, 114. As is shown, driver 116 for IGBT 90 (and associated connections) is identical to that described in connection with driver 110. Each of IGBT's 80, 90 is preferably rated to deliver a 360 Joule pulse into a 25 ohm load [at pulse repetition rate of 1 per 5 seconds], and is also preferably rated to withstand 1200 volts in the OFF condition. One such IGBT is type is IXGH25N120A available from IXYS. To prevent unbalanced voltage between IGBT's 80, 90 in the OFF condition, resistors 120, 122 are connected in series with each other and in parallel as a voltage divider across the series connection of IGBT's 80, 90. The resistance of each resistor 120, 122 is preferably 3 mega ohms.

By adding additional IGBT's or by using IGBT's having higher current and voltage limits, the circuit can output each phase successfully at any current or voltage level. Specifically, this allows the switching from phase 1 to phase 2 at voltage levels greater than 1000 volts. For example, by putting four 1200 volt IGBT's in series for each phase, the circuit can withstand (or hold off) 4800 volts per phase or a total of 9600 volts.

The operation of selector subsystem 60 is as follows. When it is desired to turn phase selector switch 62 ON, a low level signal is generated by select phase control 66, providing a logic ON signal on lead 112 and removing a logic OFF signal on lead 114. Drivers 110 and 116 may be any type of voltage isolating driver circuits sufficient to meet the speed and voltage requirements of the defibrillator system. When it is time to turn off phase 1, IGBT's 80 and 90 are closed thus halting the output to the patient without dumping the charge through an auxiliary SCR dumping circuit. The same is done for phase 2. During the time that the current flows through the IGBT's, peak currents are all within the safe operating areas.

Because dumping the charge in capacitor banks 40 and 42 is not needed to change phases, any dumping circuitry desired can be constructed from non-high speed components because time is not critical. This greatly reduces the cost of the components required.

DESCRIPTION OF THE PRESENT INVENTION

The present invention is a fast isolated IGBT driver circuit for truncating waveforms at any point during the delivery to a patient. The present invention will be described in detail with respect to FIG. 6, however, reference will also be made to FIGS. 4 and 5.

Figure 6:
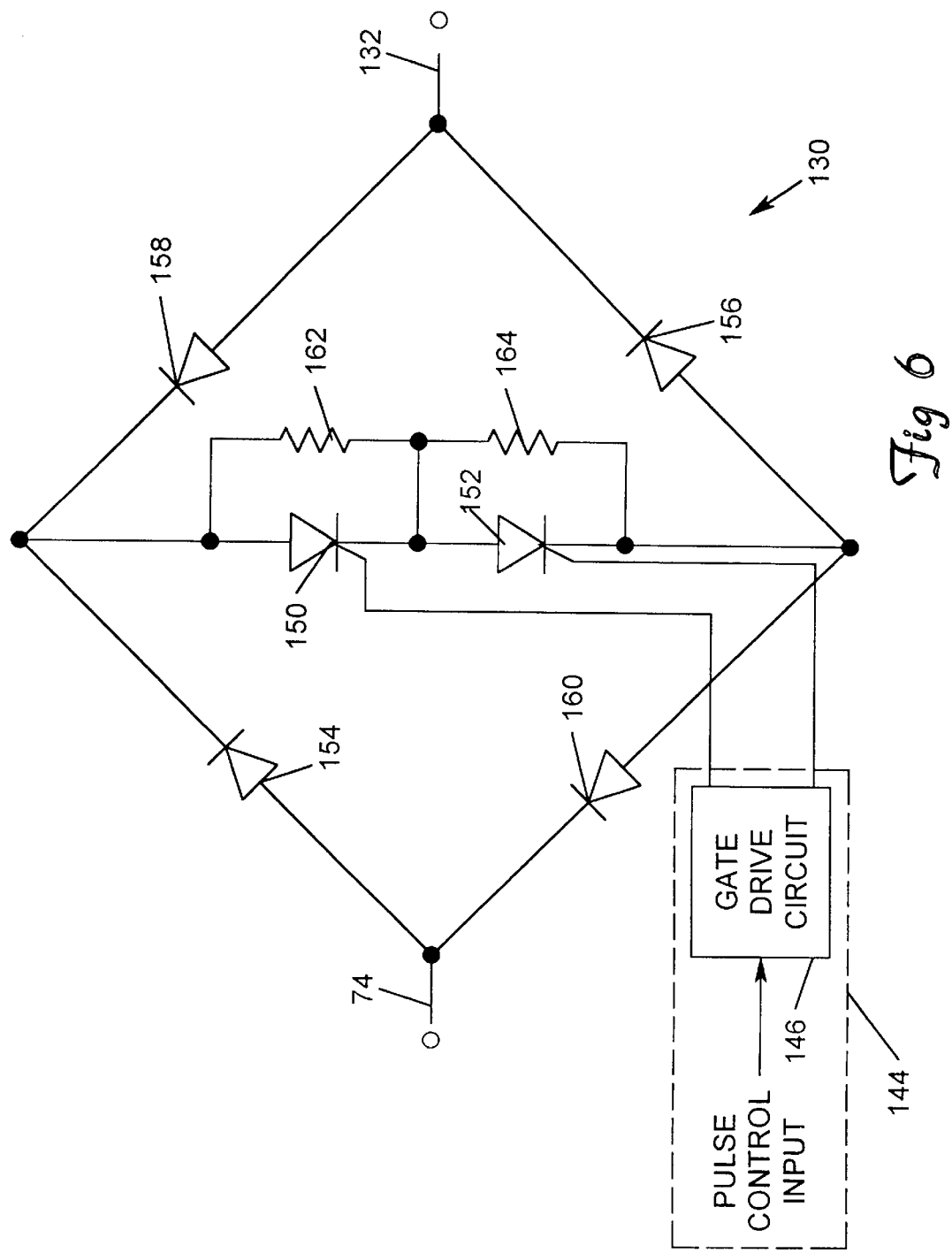
FIG. 6 is a schematic diagram of a fast isolated insulated gate bipolar transistor (IGBT) driver according to the present invention.

FIG. 6 illustrates the phase select drivers 64 from FIG. 4 which are also illustrated at 110 and 116 in FIG. 5. As previously stated, the drivers drive the selector circuits to activate or truncate waveforms in an AED. A single fast isolation driver (110 and 116) according to the present invention is illustrated in FIG. 6. As illustrated in FIG. 6, the driver of the preferred embodiment is comprised of two identical portions, upper portion 150 and lower portion 152 for reasons to be described below.

Upper portion 150 has first and second field effect transistor (FET) drivers 154, 156, respectively that comprise an input circuit portion. In the preferred embodiment of the present invention, these drivers are high current, low impedance drivers. An input line 158 is provided to driver 154 and an input line 160 is provided to driver 156. In the preferred embodiment of the present invention, inputs 158 and 160 receive a 30 KHz, 50% duty cycle signal from select phase control circuit 66 as illustrated in FIG. 5. Impedance driver 154 has an output 162 while impedance driver 156 has an output 164. An isolation transformer 166 is provided having a primary coil 168 and a secondary coil 170. Secondary coil 170 has first and second output terminals 172, 174 respectively. In the preferred embodiment of the present invention, isolation transformer 166 is a one to one transformer.

Biasing circuitry 175 is provided, connected to transformer 166. Biasing circuitry 175 is used to bias the IGBT as will be described in detail below. An N-type field effect transistor (FET) 176 is provided and is connected across secondary coil 170 of transformer 166. FET 176 has a gate 178, a source 180 and a drain 182. Source 180 is connected to first output terminal 172 of transformer 166 at node 184. A resistor 186 is provided and is connected between gate 178 and output terminal 174 at node 188. A P-type FET 190 is also provided having a gate 192, a source 194 and a drain 196. Source 194 is connected to node 184 while gate 192 is connected to node 188 through a resistor 198. In the preferred embodiment of the present invention, resistors 186 and 198 are one kiliohm resistors, however, it should be noted that greater or lesser resistance can also be used without departing from the spirit or scope of the present invention.

A pair of diodes 200 and 202 are provided having anodes 204, 206 and cathodes 208, 210, respectively as illustrated in FIG. 6. Anode 204 of diode 200 is connected to drain 182 while anode 206 is connected to cathode 208 at node 212. Cathode 210 is connected to drain 196 of FET 190. A capacitor 214 is connected between nodes 212 and 188. In the preferred embodiment of the present invention, capacitor 212 is a 0.1 microfarad capacitor, however, it should be noted that larger or smaller capacitors could also be used without departing from the spirit or scope of the present invention. An insulated gate bipolar transistor (IGBT) 216 is provided having a gate 218, a collector 220 and an emitter 222. Gate 218 is connected to node 212, emitter 222 is connecting to node 188 and collector 220 is output to isolator circuit 56, as illustrated in FIG. 4.

As previously stated, the lower portion 152 mirrors upper portion 150. Accordingly, each element in lower portion 152 is identified with the same element number as in upper portion 150 with the addition of a prime.

In the preferred embodiment of the present invention, the maximum output defibrillation pulse is approximately 2,400 volts. In order to effectively handle this voltage, the IGBT's selected are rated at approximately 1200 volts breakdown. As can be seen, IGBT 216 and 216' are connected in series which allows approximately 2400 volts breakdown to be handled effectively. This allows the output waveform to be interrupted at any point in the delivery of energy to the patient which also allows a selection of either of the two phases when constructing the biphasic waveform output. Additional IGBT's could be also be placed in series for higher voltage levels.

The operation of the circuit of FIG. 6 will be described in detail with regards to upper portion 150, however, it should be understood that lower portion 152 operates just the same. When driver 154 is receiving a positive input signal and driver 156 is receiving a zero potential signal, the signal at output 164 remains zero while the signal at 162 is pulsing at a positive 12 volts. As stated before, isolation transformer 166 is a one to two transformer, therefore, output terminal 172 will be positive compared to output terminal 174. In this situation, gate 178 is negative with respect to source 180 which causes FET 176 to be turned on. At the same time, gate 192 is negative with respect to source 194 which turns FET 190 off. With FET 176 on, diode 200 is forward biased and the charge of energy from transformer 166 is stored in capacitor 214. This charge is replenished at each pulse and appears as direct current (DC) forward biasing IGBT 216 causing it to be turned on. With IGBT 216 on, a defibrillation pulse is allowed to be delivered to a patient.

When the signal and input 160 goes high, while the signal at 158 goes low, output 162 goes to zero while output 164 is pulsing at 12 volts. This causes a negative pulse to appear at output terminal 172 with respect to output terminal 174. When this occurs, FET 176 is turned off and FET 190 is forward biased, turning it on. The negative voltage at source 194 is felt at cathode 210 of diode 202 which passes it along to capacitor 214 and gate 218. Again this appears as DC and has the effect of making gate 218 negative with respect to emitter 222 which turns IGBT 216 off. When IGBT 216 shuts off, the defibrillation waveform is truncated.

The amount of energy transferred through the transformer with each pulse is enough to cause this action to occur at a very fast rate. The IGBT gate signal can switch from plus 20 V to minus 20 V and because of the negative gate bias, the time for IGBT turn off is reduced to be in the range of 200 to 400 nanoseconds. In one embodiment, the turn off time is reduced to less than 320 nanoseconds and preferably to about 300 nanoseconds. This is needed to truncate the defibrillator output pulse by turning the IGBTs OFF as fast as is practical to minimize the trajectory time through the active region.

The invention is not to be taken as limited to all of the details thereof as modifications and variations thereof may be made without departing from the spirit or scope of the invention.

I claim:

1. Fast isolation driver system comprising:

an input circuit for receiving input signals from a plurality of input lines;

an isolation transformer connected to the input circuit wherein the isolation transformer has first and second output terminals;

biasing circuitry connected to the first and second output terminals wherein the biasing circuitry has a first FET having its source connected to the first output terminal of the isolation transformer, its gate connected to the second output terminal of the isolation transformer, and its drain connected to a first diode, and wherein the biasing circuitry also has a second FET having its source connected to the first output terminal of the isolation transformer, its gate connected to the second output terminal of the isolation transformer, and its drain connected to a second diode; and an insulated gate bipolar transistor (IGBT) having its gate connected to the drains of the first and second FETs of the biasing circuitry, through the first and second diodes, and its emitter connected to the second output terminal wherein the IGBT switches between operational states in response to the biasing circuitry.

2. The system as in claim 1 wherein the input circuitry comprises first and second field effect transistor (FET) drivers.

3. The system as in claim 1 wherein the isolation transformer is a one to one transformer.

4. The system as in claim 1 wherein the first diode is connected to the IGBT at its cathode and the second diode is connected to the IGBT at its anode at a first node.

5. The system as in claim 4 wherein a capacitive storage device is provided connected between the first node and the second output terminal of the isolation transformer.

6. The system as in claim 1 wherein the IGBT switches between operational states within the range of 200 to 400 nanoseconds.

7. The system as in claim 1 wherein the IGBT switches between operational states in less than 320 nanoseconds.

8. A fast isolation driver system for use in external defibrillators, the system comprising:

a first input circuit for receiving first and second input signals;

a first isolation transformer connected to the first input circuit wherein the first isolation transformer has first and second output terminals;

a first biasing circuit connected to the first and second output terminals of the first isolation transformer;

a first insulated gate bipolar transistor (IGBT) connected to the first biasing circuit;

a second input circuit connected in parallel with the first input circuit, wherein the second input circuit receives the first and second input signals;

a second isolation transformer connected to the second input circuit wherein the second isolation transformer has first and second output terminals;

a second biasing circuit connected to the first and second output terminals of the second isolation transformer;

a second insulated gate bipolar transistor (IGBT) connected to the second biasing circuit; and wherein the first and second IGBT are connected in series and wherein the first and second IGBTs switch between operational states in response to the first and second biasing circuits.

9. The system as in claim 8 wherein the first biasing circuit has a first FET having its source connected to the first output terminal of the first isolation transformer, its gate connected to the second output terminal of the first isolation transformer and its drain connected to the first IGBT through a first diode, and wherein the first biasing circuitry also has a second FET having its source connected to the first output terminal of the first isolation transformer, its gate connected to the second output terminal of the first isolation transformer and its drain connected to the first IGBT through a second diode, and wherein the second biasing circuit has a first FET having its source connected to the first output terminal of the second isolation transformer, its gate connected to the second output terminal of the second isolation transformer and its drain connected to the second IGBT through a third diode, and wherein the second biasing circuit also has a second FET having its source connected to the first output terminal of the second isolation transformer, its gate connected to the second output terminal of the second isolation transformer and its drain connected to the second IGBT through a fourth diode.

10. The system as in claim 9 wherein the first diode of the first biasing circuit is connected to the first IGBT at its cathode and the second diode of the first biasing circuit is connected to the first IGBT at its anode at a first node and wherein the third diode of the second biasing circuit is connected to the second IGBT at its cathode and the fourth diode of the second biasing circuit is connected to the second IGBT at its anode at a second node.

11. The system as in claim 10 wherein a first capacitive storage device is provided connected between the first node and the second output terminal of the first isolation transformer and wherein a second capacitive storage device is provided connected between the second node and the second output terminal of the second isolation transformer.

12. The system as in claim 8 wherein the first and second IGBTs switch between operational states within the range of 200 to 400 nanoseconds.

13. The system as in claim 8 wherein the first and second IGBTs switch between operational states in less than 320 nanoseconds.

* * * * *